United States Patent [19]

Ruoslahti et al.

[11] Patent Number: 5,583,103
[45] Date of Patent: Dec. 10, 1996

[54] INHIBITION OF TRANSFORMING GROWTH FACTOR BETA ACTIVITY

[75] Inventors: Erkki I. Ruoslahti, Rancho Santa Fe; Yu Yamaguchi, San Diego, both of Calif.

[73] Assignee: La Jolla Cancer Research Foundation, La Jolla, Calif.

[21] Appl. No.: 212,311

[22] Filed: Mar. 14, 1994

Related U.S. Application Data

[63] Continuation of Ser. No. 50,762, Apr. 20, 1993, abandoned, which is a continuation of Ser. No. 467,888, Jan. 22, 1990, abandoned, which is a continuation-in-part of Ser. No. 212,702, Jun. 28, 1988, abandoned.

[51] Int. Cl.$^6$ .................. A61K 38/19; C07K 14/495
[52] U.S. Cl. .................. 514/8; 514/2; 530/350; 530/399; 530/380
[58] Field of Search .................. 530/399, 380, 530/350, 300; 514/8, 2; 435/7.1

[56] References Cited

FOREIGN PATENT DOCUMENTS

282317A2  9/1988  European Pat. Off. .
282317    10/1988  European Pat. Off. .

OTHER PUBLICATIONS

Socher et al 1987 PNAS 84:8829.
Titani et al 1987 PNAS 84:5610.
Sporn et al 1986 Science 233:532.
Chiefetz et al. "The Transforming Growth Factor β System . . ." Cell vol. 48 pp. 409–415.
Border, Wayne A. et al. "Extracellular Matrix and Glomerular Disease." Seminars in Nephrology. 9:307–317 (1989).
Andres et al., Membrane–anchored and Soluble Forms of Betaglycan, a Polymorphic Proteoglycan that Binds Transforming Growth Factor–Beta. J. Cell. Biol. 109:3137–3145 (1989).
Kanzaki et al., TGF–Beta 1 Binding Protein: A Component of the Large Latent Complex of TGF–Beta1 with Multiple Repeat Sequences. Cell 61:1051–1061 (1990).
Cheifetz et al., Heterodimeric Transforming Growth Factor Beta J. Biol. Chem. 263:10783–10789 (1988a).
Cheifetz et al., The Transforming Growth Factor–Beta Receptor Type III is a Membrane Proteoglycan. J. Biol. Chem. 263:16984–16991 (1988b).
Fisher et al., Deduced Protein Sequence of Bone Small Proteoglycan I (Biglycan) shows Homology with Proteoglycan II (Decorin) and Several Nonconnective Tissue Proteins in a Variety of Species. J. Biol. Chem. 264:4571–4576 (1989).
Patthy, L., Detecting Homology of Distantly Related Proteins with Consensus Sequences. J. Mol. Biol. 198:567–577 (1987).
Bassols and Massague, Transforming Growth Factor Beta Regulates the Expression and Structure of Extracellular Matrix Chondroitin/ Dermatan Sulfate Proteoglycans. J. Biol. Chem. 263:3039–3045 (1988).

Segarini and Seyedin, The High Molecular Weight Receptor to Transforming Growth Factor–Beta Contains Glycosaminoglycan Chains. J. Biol. Chem. 263:8366–8370 (1988).
Cheifetz et al., The Transforming Growth Factor–Beta System, a Complex Pattern of Cross–Reactive Ligands and Receptors. Cell 48:409–415 (1987).
Ishihara et al., Involvement of Phosphatidylinositol and Insulin in the Coordinate Regulation of Proteoheparan Sulfate Metabolism and Hepatocyte Growth. J. Biol. Chem. 262:4706–4716 (1987).
Day et al., Molecular Cloning and Sequence Analysis of the cDNA for Small Proteoglycan II of Bovine Bone. Biochem. J. 248:801–805 (1987).
Fritze et al., An Antiproliferative Heparin Sulfate Species Produced by Postconfluent Smooth Muscle Cells. J. Cell Biol. 100:1041–1049 (1985).
Krusius and Ruoslahti, Primary Structure of an Extracellular Matrix Proteoglycan Core Protein Deduced from Cloned cDNA. Proc. Natl. Acad. Sci. USA 83:7683–7687 (1986).
Castellot et al., Glomerular Endothelial Cells Secrete a Heparinlike Inhibitor and a Peptide Stimulator of Mesangial Cell Proliferation. Am. J. Pathol. 125:493–500 (1986).
Castellot et al., Inhibition of Vascular Smooth Muscle Cell Growth by Endothelial Cell–Derived Heparin. J. Biol. Chem. 257:11256–11260 (1982).
Vogel et al., Specific Inhibition of Type I and Type II Collagen Fibrillogenesis by the Small Proteoglycan of Tendon. Biochem. J. 223:587–597 (1984).
Massague and Like, Cellular Receptors for Type Beta Transforming Growth Factor. J. Biol. Chem. 260:2636–2645 (1985).
Brennan, M. et al., Effect of a Proteoglycan Produced by Rat Tumor Cells on Their Adhesion to Fibronectin–Collagen Substrata$^1$, Cancer Research 43:4302–4307 (1983).
Brennan, M. et al., Chondroitin/Dermatan Sulfate Proteoglycan in Human Fetal Membranes, J. of Biol. Chem. 259:13742–13750 (1984).
Kresse, H. et al., Glycosaminoglycan–Free Small Proteoglycan Core Protein Secreted by Fibroblasts from a Patient with a Syndrome Resembling Progeroid, Am. J. Hum. Genet. 41, (1987).
Pearson, C. et al., The $NH_2$–Terminal Amino Acid Sequence of Bovine Skin Proteodermatan Sulfate, The Journal of Biological Chemistry 258:15101–15104 (1983).
Ruoslahti, E., Structure and Biology of Proteoglycans, Ann. Rev. Cell Biol. 4:229–255 (1988).

(List continued on next page.)

*Primary Examiner*—Robert A. Wax
*Assistant Examiner*—K. Cochrane Carlson
*Attorney, Agent, or Firm*—Campbell & Flores LLP

[57] ABSTRACT

The present invention provides a method of inhibiting an activity of TGFβ comprising contacting the TGFβ with a purified decorin. In a specific embodiment, the present invention relates to the ability of decorin, a 40,000 dalton protein that usually carries a glycosaminoglycan chain, to bind TGFβ. The invention also provides a novel cell regulatory factor designated MRF. Also provided are methods of identifying, detecting and purifying cell regulatory factors and proteins which bind and affect the activity of cell regulatory factors.

6 Claims, 8 Drawing Sheets

OTHER PUBLICATIONS

Yamaguchi, Y. and Ruoslahti, E., Expression of Human Proteoglycan in Chinese Hamster Ovary Cells Inhibits Cell Proliferation, Nature 336:244–246 (1988).

Yamaguchi, Y. et al., Negative Regulation of Transforming Growth Factor-$\beta$ by the Proteoglycan Decorin, Nature 346:281–284 (1990).

Ishiharat, Masayuki "Involvement of Phosphatidylinositol and insulin in the Coordinate Regulation of Proteoheparan Sulfate Metabolism and Hepatocyte Growth." J. Biol. Chem. 262:4708–4716 (1987).

Iozzo, Renato V. "Neoplastic Modulation of Extracellular Matrix: Stimulation of Chondroitin Sulfate Proteoglycan and Hyaluronic Acid Synthesis in Co–Cultures of Human Colon Carcinoma and Smooth Muscle Cells." J. Cell. Biochem. 39:355–378 (1989).

INHIBITION OF TRANSFORMING GROWTH FACTOR BETA ACTIVITY

This invention was made with support of government grants CA 30199, CA 42507 and CA 28896 from the National Cancer Institute. Therefore, the United States government may have rights in the invention.

This application is a continuation of application Ser. No. 08/050,762, filed Apr. 20, 1993, now abandoned, which is a continuation of application Ser. No. 07/467,888, filed on Jan. 22, 1990, now abandoned, which is a continuation of application Ser. No. 07/212,702, filed Jun. 28, 1988 now abandoned.

FIELD OF INVENTION

This invention relates to cell biology and more specifically to the control of cell proliferation.

BACKGROUND OF THE INVENTION

Proteoglycans are proteins that carry one or more glycosaminoglycan chains. The known proteoglycans carry out a wide variety of functions and are found in a variety of cellular locations. Many proteoglycans are components of extracellular matrix, where they participate in the assembly of cells and effect the attachment of cells to the matrix.

Decorin, also known as PG-II or PG-40, is a small proteoglycan produced by fibroblasts. Its core protein has a molecular weight of about 40,000 daltons. The core has been sequenced (Krusius and Ruoslahti, Proc. Natl. Acad. Sci. USA 83:7683 (1986); Day et al. Biochem. J. 248:801 (1987), both of which are incorporated herein by reference) and it is known to carry a single glycosaminoglycan chain of a chondroitin sulfate/dermatan sulfate type (Pearson, et al., J. Biol. Chem. 258:15101 (1983), which is incorporated herein by reference). The only previously known function for decorin is binding to type I and type II collagen and its effect on the fibril formation by these collagens (Vogel, et al., Biochem. J. 223:587 (1984); Schmidt et al., J. Cell Biol. 104:1683, (1987)). Two proteoglycans, biglycan (Fisher et al., J. Biol. Chem. 264:4571 (1989)) and fibromodulin, (Oldberg et al., Embo J. 8:2601, (1989) have core proteins the amino acid sequences of which are closely related to that of decorin and they, together with decorin, can be considered a protein family. Each of their sequences is characterized by the presence of a leucine-rich repeat of about 24 amino acids. Several other proteins contain similar repeats. Together all these proteins form a superfamily of proteins (Ruoslahti, Ann. Rev. Cell Biol. 4:229, (1988); McFarland et al., Science 245:494 (1989)).

Transforming growth factor β's (TGFβ) are a family of multifunctional cell regulatory factors produced in various forms by many types of cells (for review see Sporn et al., J. Cell Biol. 105:1039, (1987)). Five different TGFβ's are known, but the functions of only two, TGFβ-1 and TGFβ-2, have been characterized in any detail. TGFβ's are the subject of U.S. Pat. Nos. 4,863,899; 4,816,561; and 4,742,003 which are incorporated by reference. TGFβ-1 and TGFβ-2 are publicly available through many commercial sources (e.g. R & D Systems, Inc., Minneapolis, Minn.). These two proteins have similar functions and will be here collectively referred to as TGFβ. TGFβ binds to cell surface receptors possessed by essentially all types of cells, causing profound changes in them. In some cells, TGFβ promotes cell proliferation, in others it suppresses proliferation. A marked effect of TGFβ is that it promotes the production of extracellular matrix proteins and their receptors by cells (for review see Keski-Oja et al., J. Cell Biochem 33:95 (1987); Massague, Cell 49:437 (1987); Roberts and Sporn in "Peptides Growth Factors and Their Receptors" [Springer-Verlag, Heidelberg] in press (1989)).

While TGFβ has many essential cell regulatory functions, improper TGFβ activity can be detrimental to an organism. Since the growth of mesenchyme and proliferation of mesenchymal cells is stimulated by TGFβ, some tumor cells may use TGFβ as an autocrine growth factor. Therefore, if the growth factor activity of TGFβ could be prevented, tumor growth could be controlled. In other cases the inhibition of cell proliferation by TGFβ may be detrimental, in that it may prevent healing of injured tissues. The stimulation of extracellular matrix production by TGFβ is important in situations such as wound healing. However, in some cases the body takes this response too far and an excessive accumulation of extracellular matrix ensues. An example of excessive accumulation of extracellular matrix is glomerulonephritis, a disease with a detrimental involvement of TGFβ.

Thus, there exists a critical need to develop compounds that can modulate the effects of cell regulatory factors such as TGFβ. The present invention satisfies this need and provides related advantages.

SUMMARY OF THE INVENTION

The present invention provides a method of inhibiting an activity of a cell regulatory factor comprising contacting the cell regulatory factor with a purified polypeptide, wherein the polypeptide comprises a cell regulatory factor binding domain of a protein and wherein the protein is characterized by a leucine-rich repeat of about 24 amino acids. In a specific embodiment, the present invention relates to the ability of decorin, a 40,000 dalton protein that usually carries a glycosaminoglycan chain, to bind TGFβ. The invention also provides a novel cell regulatory factor designated Morphology Restoring Factor, (MRF). Also provided are methods of identifying, detecting and purifying cell regulatory factors and proteins which bind and affect the activity of cell regulatory factors.

BRIEF DESCRIPTION OF THE FIGURES

(FIG. 2A) Fractionation of [$^{125}$I]-TGFβ1 by decorin-Sepharose affinity chromatography. [$^{125}$I]TGFβ1 ($5\times10^5$ cpm) was incubated in BSA-coated polypropylene tubes with 0.2 ml of packed decorin-Sepharose (●) or gelatin-Sepharose (0) in 2 ml of PBS pH 7.4, containing 1M NaCl and 0.05% Tween 20. After overnight incubation, the affinity matrices were transferred into BSA-coated disposable columns (Bio Rad) and washed with the binding buffer. Elution was effected first with 3M NaCl in the binding buffer and then with 8M urea in the same buffer.

(FIG. 2B) Analysis of eluents of decorin-Sepharose affinity chromatography by SDS-polyacrylamide gel under non-reducing conditions. Lane 1: the original [$^{125}$I]-labeled TGFβ1 sample; lanes 2–7: flow through and wash fractions; lanes 8–10: 3M NaCl fractions; lanes 11–14: 8M urea fractions. Arrows indicate the top and bottom of the 12% separating gel.

(FIG. 3A) Competition of [$^{125}$I]TGFβ1 binding to decorin-coated microtiter wells by recombinant decorin (●), decorin isolated from bovine skin (PGII) (■), biglycan isolated from bovine articular cartilage (PGI) (▲), chicken cartilage proteoglycan (o), and BSA (□). Each point represents the mean of duplicate determinants.

(FIG. 3B) Competition of [$^{125}$I]TGFβ1 binding with chondroitinase ABC-treated proteoglycans and BSA. The concentrations of competitors were expressed as intact proteoglycan. The symbols are the same as in FIG. 3A.

(FIG. 4A) Shows inhibition of TGFβ1-induced proliferation of CHO cells by decorin. [$^3$H]Thymidine incorporation assay was performed as described in the legend of FIG. 1 in the presence of 5 ng/ml of TGFβ-1 and the indicated concentrations of purified decorin (●) or BSA (0). At the concentration used, TGFβ-1 induced a 50% increase of [$^3$H]thymidine incorporation in the CHO cells. The data represent percent neutralization of this growth stimulation; i.e. [$^3$H]thymidine incorporation in the absence of either TGFβ1 or decorin=0%, incorporation in the presence of TGFβ but not decorin=100%. Each point shows the mean±standard deviation of triplicate samples.

(FIG. 4B) Shows neutralization of TGFβ1-induced growth inhibition in Mv1Lu cells by decorin. Assay was performed as in A except that TGFβ-1 was added at 0.5 ng/ml. This concentration of TGFβ-1 induces 50% reduction of [$^3$H]thymidine incorporation in the Mv1Lu cells. The data represent neutralization of TGFβ-induced growth inhibition; i.e. [$^3$H]thymidine incorporation in the presence of neither TGFβ or decorin=100%; incorporation in the presence of TGFβ but not decorin=0%.

DETAILED DESCRIPTION OF THE INVENTION

Figures 1A, 1B:
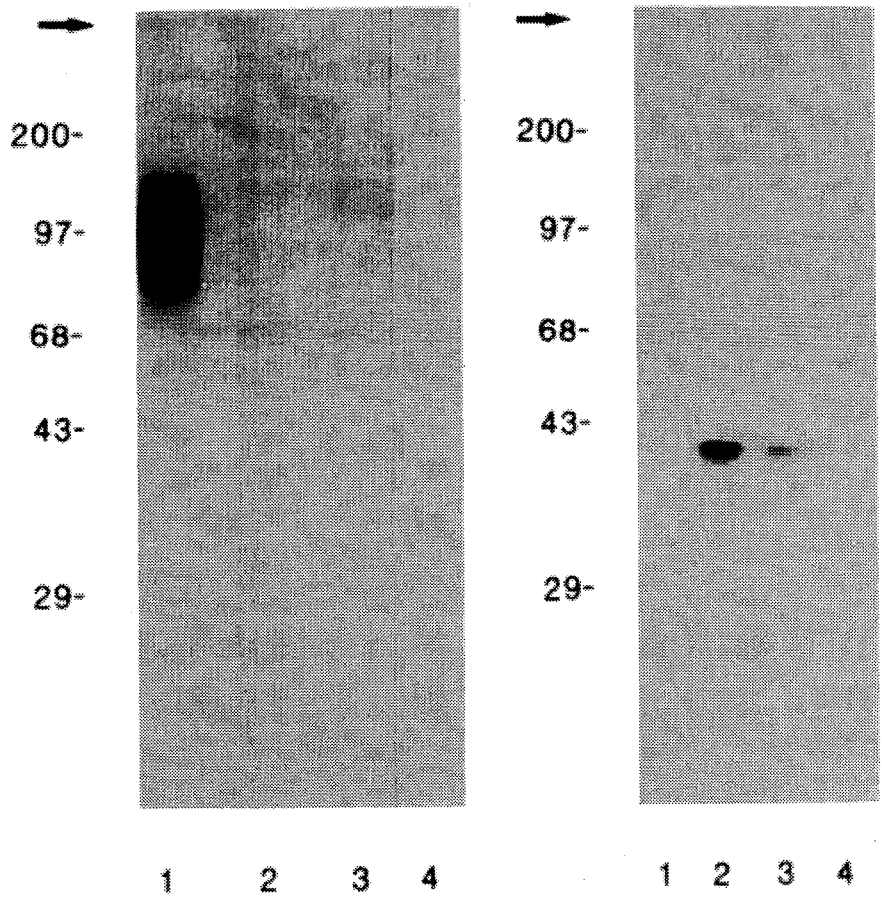
FIGS. 1A and 1B show expression of decorin cDNA containing a mutation of the serine acceptor site to alanine. COS-1 cultures were transfected with cDNA coding for wild-type decorin (lane 1), decorin in which the serine-4 residue was replaced by an alanine (lane 2), or decorin in which the serine-4 residue was replaced by a threonine (lane 3). Immunoprecipitations were performed with an anti-decorin antibody and medium which was labeled with $^{35}$S-sulfate (FIG. 1A) or $^3$H-leucine (FIG. 1B). Lane 4 shows an immunoprecipitate from mock transfected COS-1 cultures. Arrow indicates top of gel. The numbers indicate $M_r \times 10^{-3}$ for molecular weight standards.

The invention provides a method of inhibiting an activity of a cell regulatory factor comprising contacting the cell regulatory factor with a purified polypeptide, wherein the polypeptide comprises the cell regulatory factor binding domain of a protein and wherein the protein is characterized by a leucine-rich repeat of about 24 amino acids. Since diseases such as cancer result from uncontrolled cell proliferation, the invention can be used to treat such diseases.

By "cell regulatory factor" is meant a molecule which can regulate an activity of a cell. The cell regulatory factors are generally proteins which bind cell surface receptors and include growth factors. Examples of cell regulatory factors include the five TGFβ's, platelet-derived growth factor, epidermal growth factor, insulin like growth factor I and II, fibroblast growth factor, interleukin-2, nerve growth factor, hemopoietic cell growth factors (IL-3, GM-CSF, M-CSF, G-CSF, erythropoietin) and the newly discovered Morphology Restoring Factor, hereinafter "MRF". Different regulatory factors can be bound by different proteins which can affect the regulatory factor's activity. For example, TGFβ-1 is bound by decorin and biglycan, and MRF by decorin.

By "cell regulatory factor binding domain" is meant the fragment of a protein which binds to the cell regulatory factor. While the specific examples set forth herein utilize proteins, it is understood that a protein fragment which retains the binding activity is included within the scope of the invention. Fragments which retain such activity can be recognized by their ability to competitively inhibit the binding of, for example, decorin to TGFβ, or of other polypeptides containing leucine-rich repeats to their cognate growth factors. As an example, fragments can be obtained by digestion of the native polypeptide or by synthesis of fragments based on the known amino acid sequence. Such fragments can then be used in a competitive assay to determine whether they retain binding activity. For example, decorin can be attached to an affinity matrix, as by the method of Example II. Labelled TGFβ, and the fragment in question can then be contacted with the affinity matrix and the amount of TGFβ bound thereto determined.

As used herein, "decorin" refers to a proteoglycan having substantially the structural characteristics attributed to it in Krusius and Ruoslahti, supra. Human fibroblast decorin has substantially the amino acid sequence presented in Krusius and Ruoslahti, supra. "Decorin" refers both to the native composition and to modifications thereof which substantially retain the functional characteristics. Decorin core protein refers to decorin that no longer is substantially substituted with glycosaminoglycan and is included in the definition of decorin. Decorin can be rendered glycosaminoglycan-free by mutation or other means, such as by producing recombinant decorin in cells incapable of attaching glycosaminoglycan chains to a core protein.

Since the regulatory factor binding proteins each contain leucine-rich repeats of about 24 amino acids which can constitute 80% of the protein, it is likely that the fragments which retain the binding activity occur in the leucine-rich repeats. However, it is possible the binding activity resides in the carboxy terminal amino acids or the junction of the repeats and the carboxy terminal amino acids.

The invention teaches a general method whereby one skilled in the art can identify proteins which can bind to cell regulatory factors or identify cell regulatory factors which bind to a certain family of proteins. The invention also teaches a general method whereby these novel proteins or known existing proteins can be assayed to determine if they affect an activity of a cell regulatory factor. Specifically, the invention teaches the discovery that decorin and biglycan bind TGFβ-1 and MRF and that such binding can inhibit the cell regulatory functions of TGFβ-1. Further, both decorin and biglycan are about 80% homologous and contain a leucine-rich repeat of about 24 amino acids in which the arrangement of the leucine residues is conserved. As defined each repeat generally contains at least two leucine residues and can contain five or more. These proteoglycans are thus considered members of the same protein family. See Ruoslahti, supra, Fisher et al., J. Biol. Chem., 264:4571–4576 (1989) and Patthy, J. Mol. Biol., 198:567–577 (1987), all of which are incorporated by reference. Other known or later discovered proteins having this leucine-rich repeat, i.e., fibromodulin, would be expected to have a similar cell regulatory activity. The ability of such proteins to bind cell regulatory factors could easily be tested, for example by affinity chromatography or microtiter assay as set forth in Example II, using known cell regulatory factors, such as TGFβ-1. Alternatively, any later discovered cell regulatory factor could be tested, for example by affinity chromatography using one or more regulatory factor binding proteins. Once it is determined that such binding occurs, the effect of the binding on the activity of all regulatory factors can be determined by methods such as growth assays as set forth in Example III. Moreover, one skilled in the art could simply substitute a novel cell regulatory factor for TGFβ-1 or a novel leucine-rich repeat protein for decorin or biglycan in the Examples to determine their activities. Thus, the invention provides general methods to identify and test novel cell regulatory factors and proteins which affect the activity of these factors.

The invention also provides a novel purified compound comprising a cell regulatory factor attached to a purified polypeptide wherein the polypeptide comprises the cell regulatory factor binding domain of a protein and the protein is characterized by a leucine-rich repeat of about 24 amino acids.

The invention further provides a novel purified protein, designated MRF, having a molecular weight of about 20 kd, which can be isolated from CHO cells, copurifies with decorin under nondissociating conditions, separates from decorin under dissociating conditions, changes the morphology of transformed 3T3 cells, and has an activity which is not inhibited with anti-TGFβ-1 antibody. Additionally, MRF separates from TGFβ-1 in HPLC.

The invention still further provides a method of purifying a cell regulatory factor comprising contacting the regulatory factor with a protein which binds the cell regulatory factor and has a leucine-rich repeat of about 24 amino acids and to purify the regulatory factor which becomes bound to the protein. The method can be used, for example, to purify TGFβ-1 by using decorin.

The invention additionally provides a method of treating a pathology caused by a TGFβ-regulated activity comprising contacting the TGFβ with a purified polypeptide, wherein the polypeptide comprises the TGFβ binding domain of a protein and wherein the protein is characterized by a leucine-rich repeat of about 24 amino acids, whereby the pathology-causing activity is prevented or reduced. While the method is generally applicable, specific examples of pathologies which can be treated include a cancer, a fibrotic disease, and glomerulonephritis. In cancer, for example, decorin can be used to bind TGFβ-1, destroying TGFβ-1's growth stimulating activity on the cancer cell.

Finally, a method of preventing the inhibition of a cell regulatory factor is provided. The method comprises contacting a protein which inhibits an activity of a cell regulator factor with a molecule which inhibits the activity of the protein. For example, decorin could be bound by a molecule, such as an antibody, which prevents decorin from binding TGFβ-1, thus preventing decorin from inhibiting the TGFβ-1 activity. Thus, the TGFβ-1 wound healing activity could be promoted by binding TGFβ-1 inhibitors.

It is understood that modifications which do not substantially affect the activity of the various molecules of this invention including TGFβ, MRF, decorin, biglycan and fibromodulin are also included within the definition of those molecules. It is also understood that the core proteins of decorin, biglycan and fibromodulin are also included within the definition of those molecules.

The following examples are intended to illustrate but not limit the invention.

EXAMPLE I

Expression and Purification of Recombinant Decorin and Decorin Core Protein

Expression System

The 1.8 kb full-length decorin cDNA described in Krusius and Ruoslahti, Proc. Natl. Acad. Sci. USA 83:7683 (1986), which is incorporated herein by reference, was used for the construction of decorin expression vectors. For the expression of decorin core protein, cDNA was mutagenized so the fourth codon, TCT, coding for serine, was changed to ACT coding for threonine, or GCT coding for alanine. This was engineered by site-directed mutagenesis according to the method of Kunkel, Proc. Natl. Acad. Sci USA 82:488 (1985), which is incorporated herein by reference. The presence of the appropriate mutation was verified by DNA sequencing.

The mammalian expression vectors pSV2-decorin and pSV2-decorin/CP-thr4 core protein were constructed by ligating the decorin cDNA or the mutagenized decorin cDNA into 3.4 kb HindIII-Bam HI fragment of pSV2 (Mulligan and Berg, Science 209:1423 (1980), which is incorporated herein by reference).

Dihydrofolate reductase (dhfr)-negative CHO cells (CHO-DG44) were cotransfected with pSV2-decorin or pSV2-decorin/CP and pSV2dhfr by the calcium phosphate coprecipitation method. The CHO-DG44 cells transfected with pSV2-decorin are deposited with the American Type Culture Collection under Accession Number CRL 10332. The transfected cells were cultured in nucleoside-minus alpha-modified minimal essential medium (α-MEM), (GIBCO, Long Island) supplemented with 9% dialyzed fetal calf serum, 2 mM glutamine, 100 units/ml penicillin and 100 μg/ml streptomycin. Colonies arising from transfected cells were picked using cloning cylinders, expanded and checked for the expression of decorin by immunoprecipitation from $^{35}SO_4$-labeled culture supernatants. Clones expressing a substantial amount of decorin were then subjected to gene amplification by stepwise increasing concentration of methotrexate (MTX) up to 0.64 μM (Kaufman and Sharp, J. Mol. Biol. 159:601 (1982), which is incorporated herein by reference). All the amplified cell lines were cloned either by limiting dilution or by picking single MTX resistant colonies. Stock cultures of these established cell lines were kept in MTX-containing medium. Before use in protein production, cells were subcultured in MTX-minus medium from stock cultures and passed at least once in this medium to eliminate the possible MTX effects.

Alternatively, the core protein was expressed in COS-1 cells as described in Adams and Rose, Cell 41:1007, (1985), which is incorporated herein by reference. Briefly, 6-well multiwell plates were seeded with 3–5×$10^5$ cells per 9.6 $cm^2$ growth area and allowed to attach and grow for 24 hours. Cultures were transfected with plasmid DNA when they were 50–70% confluent. Cell layers were washed briefly with Tris buffered saline (TBS) containing 50 mM Tris, 150 mM NaCl pH 7.2, supplemented with 1 mM $CaCl_2$ and 0.5 mM $MgCl_2$ at 37° C. to prevent detachment. The wells were incubated for 30 minutes at 37° C. with 1 ml of the above solution containing 2 μg of closed circular plasmid DNA and 0.5 mg/ml DEAE-Dextran (Sigma) of average molecular mass of 500,000. As a control, cultures were transfected with the pSV2 expression plasmid lacking any decorin insert or mock transfected with no DNA. Culture were then incubated for 3 hours at 37° C. with Dulbecco's Modified Eagle's medium (Irvine Scientific) containing 10% fetal calf serum and 100 μM chloroquine (Sigma), after removing the DNA/TBS/DEAE-Dextran solution and rinsing the wells with TBS. The cell layers were then rinsed twice and cultured in the above medium, lacking any chloroquine, for approximately 36 hours. WI38 human embryonic lung fibroblasts were routinely cultured in the same medium.

COS-1 cultures were radiolabeled 36–48 hours after transfection with the plasmid DNAs. All radiolabeled metabolic precursors were purchased from New England Nuclear (Boston, Mass.). The isotopes used were $^{35}$S-sulfate (460 mCi/ml), L-[3,4,5-$^3$H(N)]—leucine (140 Ci/ml) and L-[$^{14}$C(U)]—amino acid mixture (product number 445E). Cultures were labeled for 24 hours in Ham's F-12 medium (GIBCO Labs), supplemented with 10% dialyzed fetal calf serum, 2 mM glutamine and 1 mM pyruvic acid, and containing 200 μCi/ml $^{35}$S-sulfate or $^3$H-leucine, or 10 μCi/ml of the $^{14}$C-amino acid mixture. The medium was collected, supplemented with 5 mM EDTA, 0.5 mM phenylmethylsulfonylfluoride, 0.04 mg/ml aprotinin and 1 μg/ml pepstatin to inhibit protease activity, freed of cellular debris by centrifugation for 20 minutes at 2,000×G and stored at −20° C. Cell extracts were prepared by rinsing the cell layers with TBS and then scraping with a rubber policeman into 1 ml/well of ice cold cell lysis buffer: 0.05M Tris-HCl, 0.5M NaCl, 0.1% BSA, 1% NP-40, 0.5% Triton X-100, 0.1% SDS, pH 8.3. The cell extracts were clarified by centrifugation for 1.5 hours at 13,000×G at 4° C.

Rabbit antiserum was prepared against a synthetic peptide based on the first 15 residues of the mature form of the human decorin core protein (Asp-Glu-Ala-Ser-Gly-Ile-Gly-Pro-Glu-Val-Pro-Asp-Asp-Arg-Asp). The synthetic peptide and the antiserum against it have been described elsewhere (Krusius and Ruoslahti, 1986 Supra.) Briefly, the peptide was synthesized with a solid phase peptide synthesizer (Applied Biosystems, Foster City, Calif.) by using the chemistry suggested by the manufacturer. The peptide was coupled to keyhole limpet hemocyanin by using N-succinimidyl 3-(2-pyridyldithio) propionate (Pharmacia Fine Chemicals, Piscataway, N.J.) according to the manufacturer's instructions. The resulting conjugates were emulsified in Freund's complete adjuvant and injected into rabbits. Further injections of conjugate in Freund's incomplete adjuvant were given after one, two and three months. The dose of each injection was equivalent to 0.6 mg of peptide. Blood was collected 10 days after the third and fourth injection. The antisera were tested against the glutaraldehyde-cross linked peptides and isolated decorin in ELISA (Engvall, Meth. Enzymol. 70:419–439 (1980)), in immunoprecipitation and immunoblotting, and by staining cells in immunofluorescence, as is well known in the art.

Immunoprecipitations were performed by adding 20 μl of antiserum to the conditioned medium or cell extract collected from duplicate wells and then mixing overnight at 4° C. Immunocomplexes were isolated by incubations for 2 hours at 4° C. with 20 μl of packed Protein A-agarose (Sigma). The beads were washed with the cell lysis buffer, with three tube changes, and then washed twice with phosphate-buffered saline prior to boiling in gel electrophoresis sample buffer containing 10% mercaptoethanol. Immunoprecipitated proteins were separated by SDS-PAGE in 7.5–20% gradient gels or 7.5% non-gradient gels as is well known in the art. Fluorography was performed by using Enlightning (New England Nuclear) with intensification screens. Typical exposure times were for 7–10 days at −70° C. Autoradiographs were scanned with an LKB Ultroscan XL Enhanced Laser Densitometer to compare the relative intensities and mobilities of the proteoglycan bands.

SDS-PAGE analysis of cell extracts and culture medium from COS-1 cells transfected with the decorin-pSV2 construct and metabolically radiolabeled with $^{35}$S-sulfate revealed a sulfated band that was not present in mock-transfected cells. Immunoprecipitation with the antiserum raised against a synthetic peptide derived from the decorin core protein showed that the new band was decorin.

Expression of the construct mutated such that the serine residue which is normally substituted with a glycosaminoglycan (serine-4) was replaced by a threonine residue by SDS-PAGE revealed only about 10% of the level of proteoglycan obtained with the wild-type construct. The rest of the immunoreactive material migrated at the position of free core protein.

The alanine-mutated cDNA construct when expressed and analyzed in a similar manner yielded only core protein and no proteoglycan form of decorin. FIGS. 1A and B show the expression of decorin (lanes 1) and its threonine-4 (lanes 3) and alanine-4 (lanes 2) mutated core proteins expressed in COS cell transfectants. $^{35}SO_4$-labeled (FIG. 1A) and $^3$H-leucine labeled (FIG. 1B) culture supernatants were immunoprecipitated with rabbit antipeptide antiserum prepared against the $NH_2$-terminus of human decorin.

Purification of Decorin and Decorin Core Protein from Spent Culture Media

Cells transfected with pSV2-decorin vector and amplified as described above and in Yamaguchi and Ruoslahti, Nature 36:244246 (1988), which is incorporated herein by reference, were grown to 90% confluence in 8 175 $cm^2$ culture flasks in nucleoside minus α-MEM supplemented with 9% dialyzed fetal calf serum, 2 mM glutamine, 100 units/ml penicillin and 100 μg/ml streptomycin. At 90% confluence culture media was changed to 25 ml per flask of nucleoside-free α-MEM supplemented with 6% dialyzed fetal calf serum which had been passed through a DEAE Sepharose Fast Flow column (Pharmacia) equilibrated with 0.25M NaCl in 0.05M phosphate buffer, pH 7.4. Cells were cultured for 3 days, spent media was collected and immediately made to 0.5 mM phenylmethylsulfonyl fluoride, 1 μg/ml pepstatin, 0.04 mg/ml aprotinin and 5 mM EDTA.

Four hundred milliliters of the spent media were first passed through gelatin-Sepharose to remove fibronectin and materials which would bind to Sepharose. The flow-through fraction was then mixed with DEAE-Sepharose pre-equilibrated in 50 mM Tris/HCl, pH 7.4, plus 0.2M NaCl and batch absorbed overnight at 4° C. with gentle mixing. The slurry was poured into a 1.6×24 cm column, washed extensively with 50 mMTris/HCl, pH 7.4, containing 0.2M NaCl and eluted with 0.2M–0.8M linear gradient of NaCl in 50 mM Tris/HCl, pH 7.4. Decorin concentration was determined by competitive ELISA as described in Yamaguchi and Ruoslahti, supra. The fractions containing decorin were pooled and further fractionated on a Sephadex gel filtration column equilibrated with 8M urea in the Tris-HCl buffer. Fractions containing decorin were collected.

The core protein is purified from cloned cell lines transfected with the pSV2-decorin/CP vector or the vector containing the alanine-mutated cDNA and amplified as described above. These cells are grown to confluency as described above. At confluency the cell monolayer is washed four times with serum-free medium and incubated in e MEM supplemented with 2 mM glutamine for 2 hours. This spent medium is discarded. Cells are then incubated with α MEM supplemented with 2 mM glutamine for 24 hours and the spent media are collected and immediately made to 0.5 mM phenylmethylsulfonyl fluoride, 1 μg/ml pepstatin, 0.04 mg/ml aprotinin and 5 mM EDTA as serum-free spent media. The spent media are first passed through gelatin-Sepharose and the flow-through fraction is then batch-absorbed to CM-Sepharose Fast Flow (Pharmacia Fine Chemicals, Piscataway, N.J.) preequilibrated in 50 mM Tris/HCl, pH 7.4 containing 0.1M NaCl. After overnight incubation at 4° C., the slurry is poured into a column, washed extensively with the preequilibration buffer and eluted with 0.1M–1M linear gradient of NaCl in 50 mM Tris/HCl, pH 7.4. The fractions containing decorin are pooled, dialyzed against 50 mM $NH_4HCO_3$ and lyophilized. The lyophilized material is dissolved in 50 mM Tris, pH 7.4, containing 8M urea and applied to a Sephacryl S-200 column (1.5×110 cm). Fractions containing decorin core proteins as revealed by SDS-polyacrylamide electrophoresis are collected and represent purified decorin core protein.

EXAMPLE II

Binding of TGFβ to Decorin a. Affinity Chromatography of TGFβ on Decorin-Sepharose Decorin and gelatin were coupled to cyanogen bromide-activated Sepharose (Sigma) by using 1 mg of protein per ml of Sepharose matrix according to the manufacturer's instructions. Commercially obtained TGFβ-1 (Calbiochem, La Jolla, Calif.) was $^{125}$I-labelled by the chloramine T method (Frolik et al., J. Biol. Chem. 259:10995–11000 (1984)) which is incorporated herein by reference and the labeled TGFβ was separated from the unreacted iodine by gel filtration on Sephadex G-25, equilibrated with phosphate buffered saline (PBS) containing 0.1% bovine serum albumin (BSA) (FIG. 2A). [$^{125}$I]-TGFβ1 ($5 \times 10^5$ cpm) was incubated in BSA-coated polypropylene tubes with 0.2 ml of packed decorin-Sepharose (574) or gelatin-Sepharose (0) in 2 ml of PBS pH 7.4, containing 1M NaCl and 0.05% Tween 20. After overnight incubation, the affinity matrices were transferred into BSA-coated disposable columns (Bio Rad) and washed with the binding buffer. Elution was effected first with 3M NaCl in the binding buffer and then with 8M urea in the same buffer. Fractions were collected, counted for radioactivity in a gamma counter and analyzed by SDS-PAGE under nonreducing condition using 12% gels.

Figure 2A:
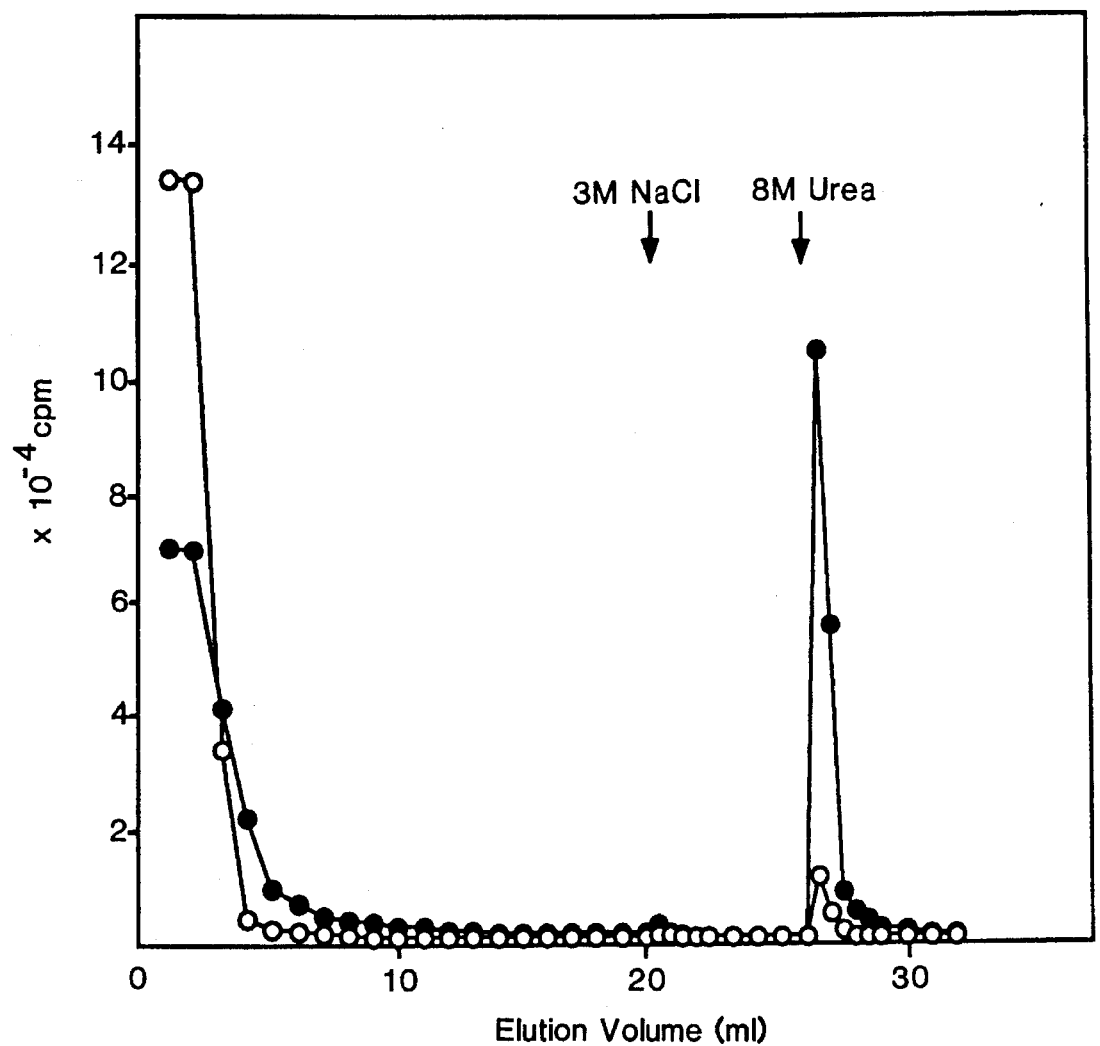
FIGS. 2A and 2B show binding of [$^{125}$I]TGFβ1 to decorin-Sepharose.
Figure 2B:
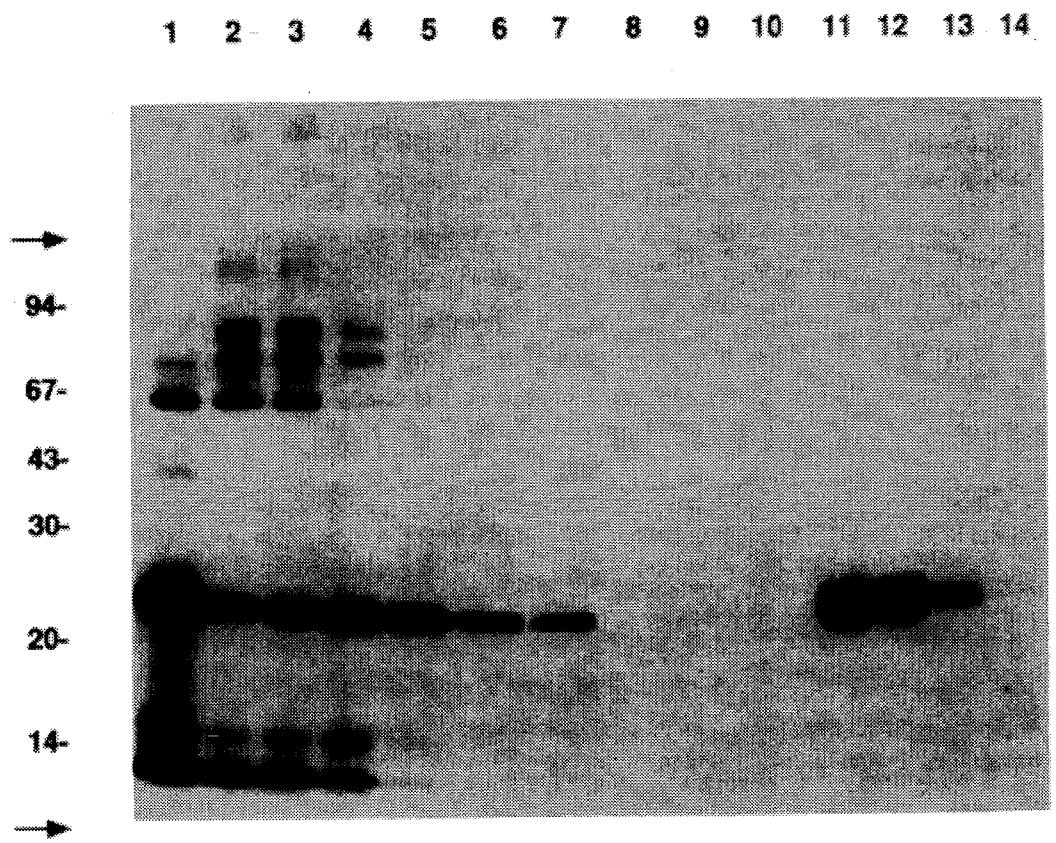

FIG. 2A shows the radioactivity profile from the two columns and the SDS-PAGE analysis of the fractions is shown in FIG. 2B. The TGFβ-1 starting material contains a major band at 25 kd. This band represents the native TGFβ-1 dimer. In addition, there are numerous minor bands in the preparation. About 20–30% of the radioactivity binds to the decorin column and elutes with 8M urea, whereas only about 2% of the radioactivity is present in the urea-eluted fraction in the control fractionation performed on gelatin-Sepharose (FIG. 2A). The decorin-Sepharose nonbound fraction contains all of the minor components and some of the 25 kd TGFβ-1, whereas the bound, urea-eluted fraction contains only TGFβ-1 (FIG. 2B). These results show that TGFβ-1 binds specifically to decorin, since among the various components present in the original TGFβ-1 preparation, only TGFβ-1 bound to the decorin-Sepharose affinity matrix and since there was very little binding to the control gelatin-Sepharose affinity matrix. The TGFβ-1 that did not bind to the decorin-Sepharose column may have been denatured by the iodination. Evidence for this possibility was provided by affinity chromatography of unlabeled TGFβ-1 as described below.

In a second experiment, unlabeled TGFβ-1 180 ng was fractionated on decorin-Sepharose as described above for $^{125}$I-TGFβ.

TGFβ-1 (180 ng) was incubated with decorin-Sepharose or BSA-agarose (0.2 ml packed volume) in PBS (pH 7.4) containing 1% BSA. After overnight incubation at 4° C., the resins were washed with 15 ml of the buffer and eluted first with 5 ml of 3M NaCl in PBS then with 5 ml of PBS containing 8M urea. Aliquots of each pool were dialyzed against culture medium without serum and assayed for the inhibition of [$^3$H]thymidine incorporation in MvlLu cells (Example III). The amounts of TGFβ-1 in each pool were calculated from the standard curve of [$^3$H]thymidine incorporation obtained from a parallel experiment with known concentration of TGFβ-1. The results show that the TGFβ-1 bound essentially quantitatively to the decorin column, whereas there was little binding to the control column (Table 1). The partial recovery of the TGFβ-1 activity may be due to loss of TGFβ-1 in the dialyses.

TABLE I

Decorin-Sepharose affinity chromatography of nonlabeled TGFβ-1 monitored by growth inhibition assay in Mv1Lu cells.

| | TGFβ-1 (ng) | |
|---|---|---|
| Elution | Decorin-Sepharose | BSA-Sepharose |
| Flow through & wash | 2.7(2.3%) | 82.0(93.9%) |
| 3 M NaCl | 2.2(1.8%) | 1.3(1.5%) |
| 8 M Urea | 116.0(95.9%) | 4.0(4.6%) | b. Binding of TGFβ-1 to Decorin in a Microtiter Assay: Inhibition by Core Protein and Byglycan The binding of TGFβ-1 to decorin was also examined in a microtiter binding assay. To perform the assay, the wells of a 96-well microtiter plate were coated overnight with 2 μg/ml of recombinant decorin in 0.1M sodium carbonate buffer, pH 9.5. The wells were washed with PBS containing 0.05% Tween (PBS/Tween) and samples containing $5 \times 10^4$ cpm of [$^{125}$I]-TGFβ-1 and various concentrations of competitors in PBS/Tween were added to each well. The plates were then incubated at 37° C. for 4 hours (at 4° C. overnight in experiments with chondroitinase ABC-digested proteoglycans), washed with PBS/Tween and the bound radioactivity was solubilized with 1% SDS in 0.2M NaOH. Total binding without competitors was about 4% under the conditions used. Nonspecific binding, determined by adding 100-fold molar excess of unlabeled TGFβ-1 over the labeled TGFβ-1 to the incubation mixture, was about 13% of total binding. This assay was also used to study the ability of other decorin preparations and related proteins to compete with the interaction.

Figure 3A:
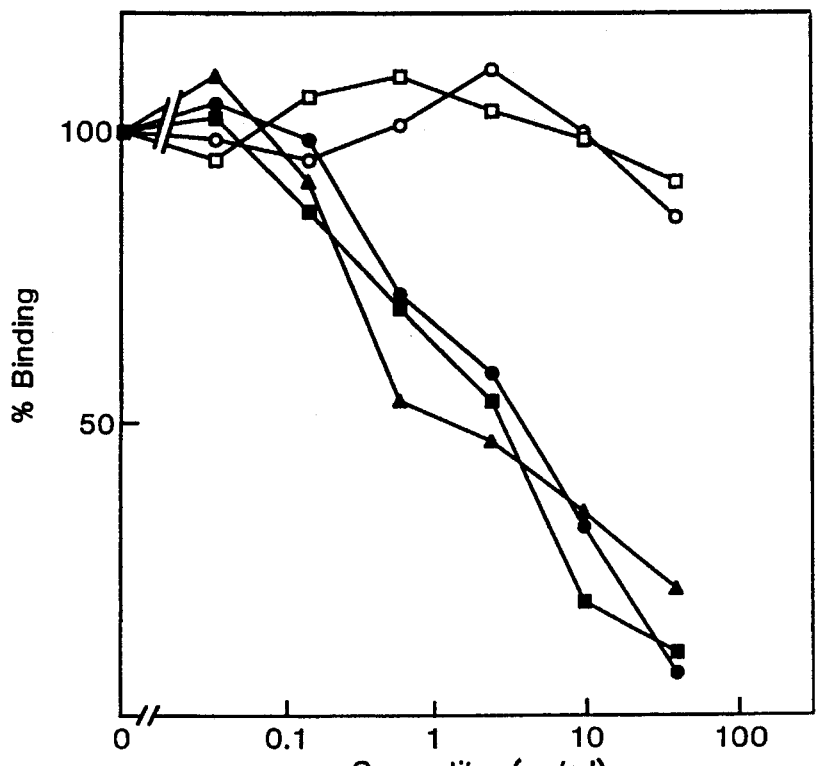
FIGS. 3A and 3B show the inhibition of binding of [$^{125}$I]TGFβ1 to decorin by proteoglycans and their core proteins.
Figure 3B:
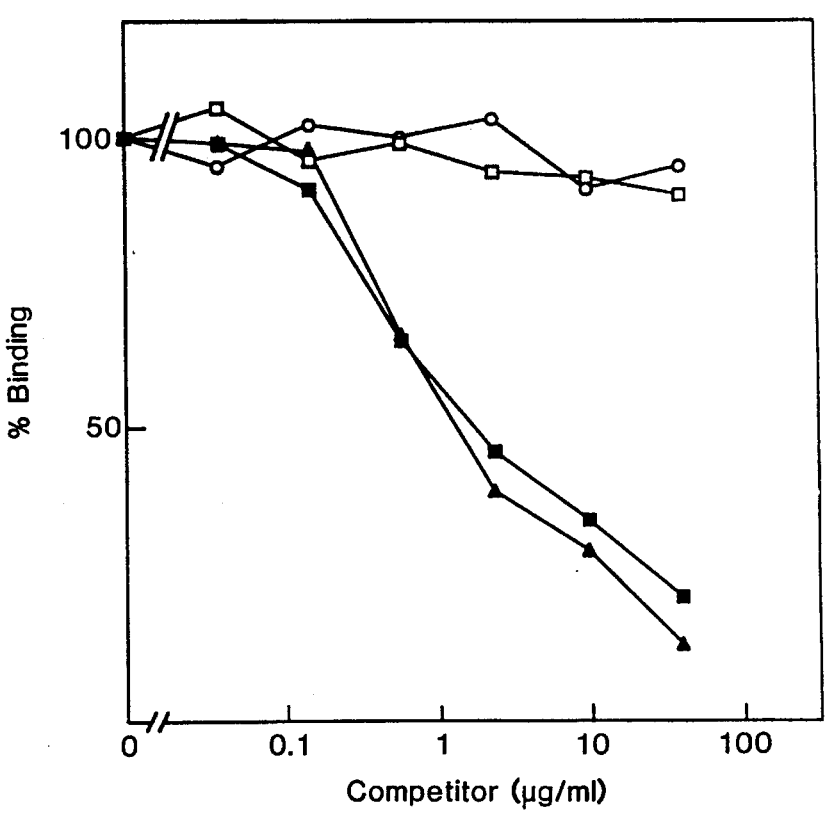

Competition of the decorin binding was examined with the following proteins (FIGS. 3A and B: symbols are indicated in the section of BRIEF DESCRIPTION OF THE FIGURES):

Decorin isolated from bovine skin and biglycan isolated from bovine articular cartilage (PGI and PGII, obtained from Dr. Lawrence Rosenberg, Monteflore Medical Center, N.Y.; and described in Rosenberg et al., J. Biol. Chem. 250:6304–6313, (1985), incorporated by reference herein), chicken cartilage proteoglycan (provided by Dr. Paul Goetinck, La Jolla Cancer Research Foundation, La Jolla, Calif., and described in Goetinck, P. F., in THE GLYCOCONJUGATES, Vol. III, Horwitz, M. I., Editor, pp. 197–217, Academic Press, NY). For the preparation of core proteins, proteoglycans were digested with chondroitinase ABC (Seikagaku, Tokyo, Japan) by incubating 500 µg of proteoglycan with 0.8 units of chondroitinase ABC in 250 µl of 0.1M Tris/Cl, pH 8.0, 30 mM sodium acetate, 2 mM PMSF, 10 mM N-ethylmalelmide, 10 mM EDTA, and 0.36 mM pepstatin for 1 hour at 37° C. Recombinant decorin and decorin isolated from bovine skin (PGII) inhibited the binding of [$^{125}$I]-TGFβ-1, as expected (FIG. 3A). Biglycan isolated from bovine articular cartilage was as effective an inhibitor as decorin. Since chicken cartilage proteoglycan, which carries many chondroitin sulfate chains, did not show any inhibition, the effect of decorin and biglycan is unlikely to be due to glycosaminoglycans. Bovine serum albumin did not shown any inhibition. This notion was further supported by competition experiments with the mutated decorin core protein (not shown) and chondroitinase ABC-digested decorin and biglycan (FIG. 3B). Each of these proteins was inhibitory, whereas cartilage proteoglycan core protein was not. The decorin and biglycan core proteins were somewhat more active than the intact proteoglycans. Bovine serum albumin treated with chondroitinase ABC did not shown any inhibition. Additional binding experiments showed that [$^{125}$I]-TGFβ-1 bound to microtiter wells coated with biglycan or its chondroitinase-treated core protein. These results show that TGFβ-1 binds to the core protein of decorin and biglycan and implicates the leucine-rich repeats these proteins share as the potential binding sites.

EXAMPLE III

Analysis of the Effect of Decorin on Cell Proliferation Stimulated or Inhibited by TGFβ-1

Figure 4A:
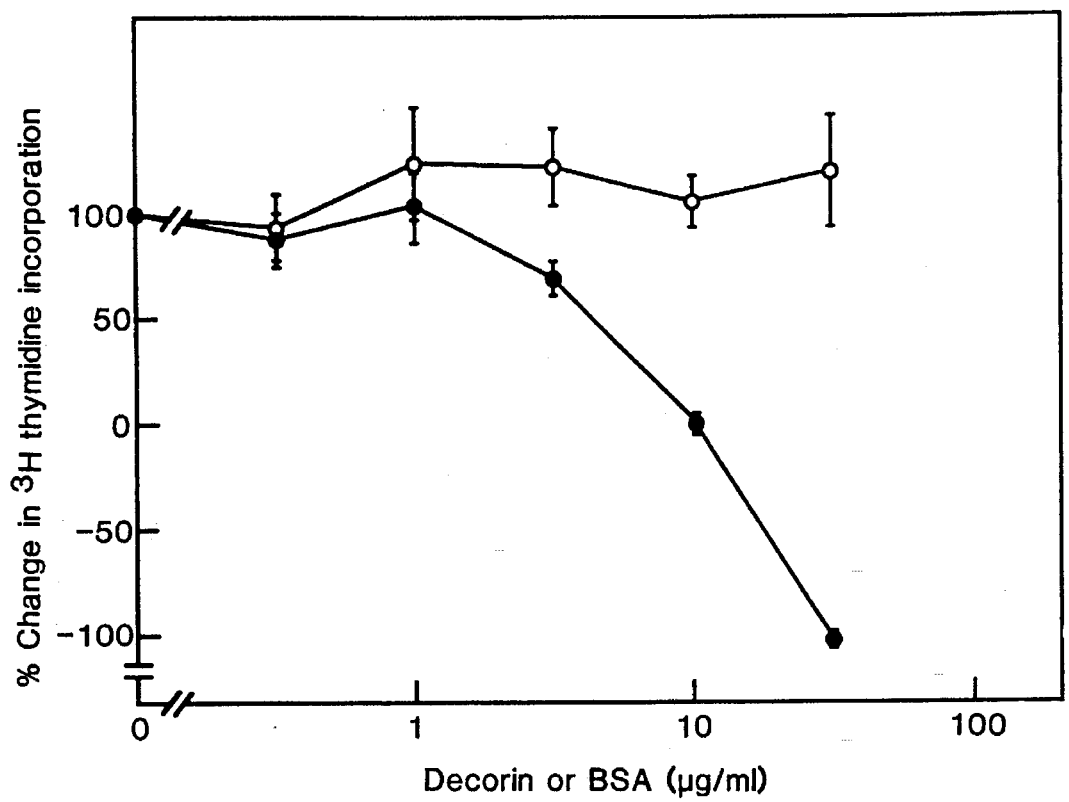
FIGS. 4A and 4B show neutralization of the growth regulating activity of TGFβ1 by decorin.

The ability of decorin to modulate the activity of TGFβ-1 was examined in [$^3$H]thymidine incorporation assays. In one assay, an unamplified CHO cell line transfected only with pSV2dhfr (control cell line A in reference 1, called CHO cells here) was used. The cells were maintained in nucleoside-free alpha-modified minimal essential medium (α-MEM, GIBCO, Long Island, N.Y.) supplemented with 9% dialyzed fetal calf serum (dFCS) and [$^3$H]thymidine incorporation was assayed as described (Cheifetz et al., Cell 48:409–415 (1987)). TGFβ-1 was added to the CHO cell cultures at 5 ng/ml. At this concentration, it induced a 50% increase of [$^3$H]thymidine incorporation in these cells. Decorin or BSA was added to the medium at different concentrations. The results are shown in FIG. 4A. The data represent percent neutralization of the TGFβ-1-induced growth stimulation, i.e., [$^3$H]thymidine incorporation, in the absence of either TGFβ-1 or decorin=0%, incorporation in the presence of TGFβ-1 but not decorin=100%. Each point shows the mean ±standard deviation of triplicate samples. Decorin (●) BSA (○).

Decorin neutralized the growth stimulatory activity of TGFβ-1 with a half maximal activity at about 5 µg/ml. Moreover, additional decorin suppressed the [$^3$H]-thymidine incorporation below the level observed without any added TGFβ-1, demonstrating that decorin also inhibited TGFβ made by the CHO cells themselves. Both the decorin-expressor and control CHO cells produced an apparently active TGFβ concentration of about 0.25 ng/ml concentration into their conditioned media as determined by the inhibition of growth of the mink lung epithelial cells. (The assay could be performed without interference from the decorin in the culture media because, as shown below, the effect of TGFβ on the mink cells was not substantially inhibited at the decorin concentrations present in the decorin-producer media.)

Figure 4B:
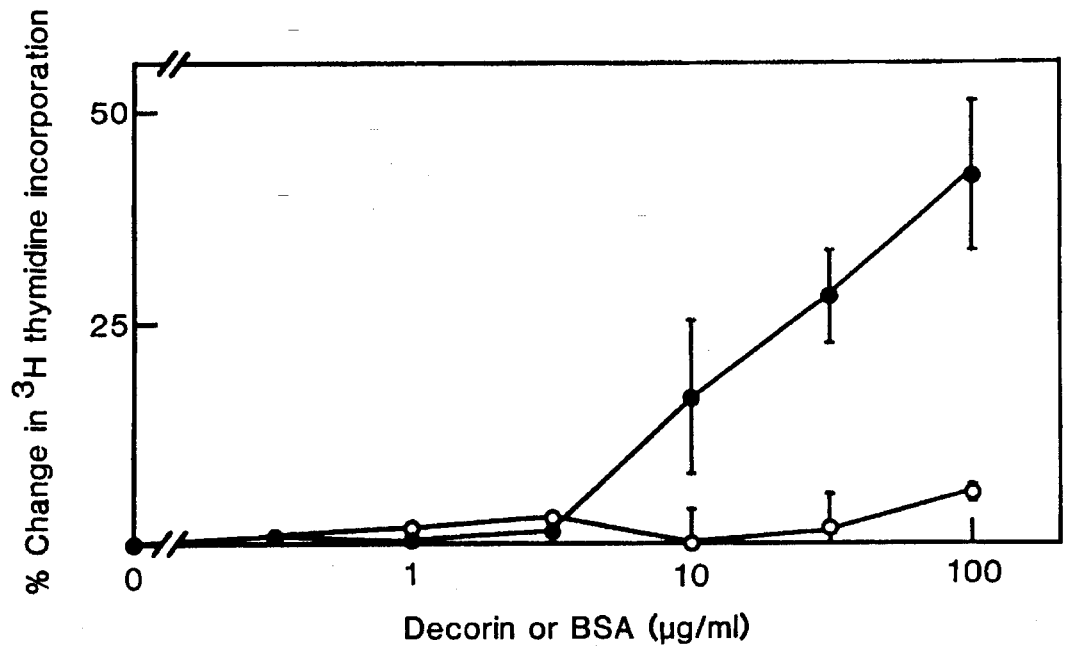

Experiments in MvLu mink lung epithelial cells (American Type Culture Collection CCL64) also revealed an effect by decorin on the activity of TGFβ-1. FIG. 4B shows that in these cells, the growth of which is measured by thymidine incorporation, had been suppressed by TGFβ-1. Assay was performed as in FIG. 4A, except that TGFβ-1 was added at 0.5 ng/ml. This concentration of TGFβ induces 50% reduction of [$^3$H]-thymidine incorporation in the Mv1Lu cells. The data represent neutralization of TGFβ-induced growth inhibition; i.e., [$^3$H]-thymidine incorporation in the presence of neither TGFβ or decorin=100%; incorporation in the presence of TGFβ but not decorin=0%.

EXAMPLE IV

New Decorin-Binding Factor that Controls Cell Spreading and Saturation Density

Figure 5A:
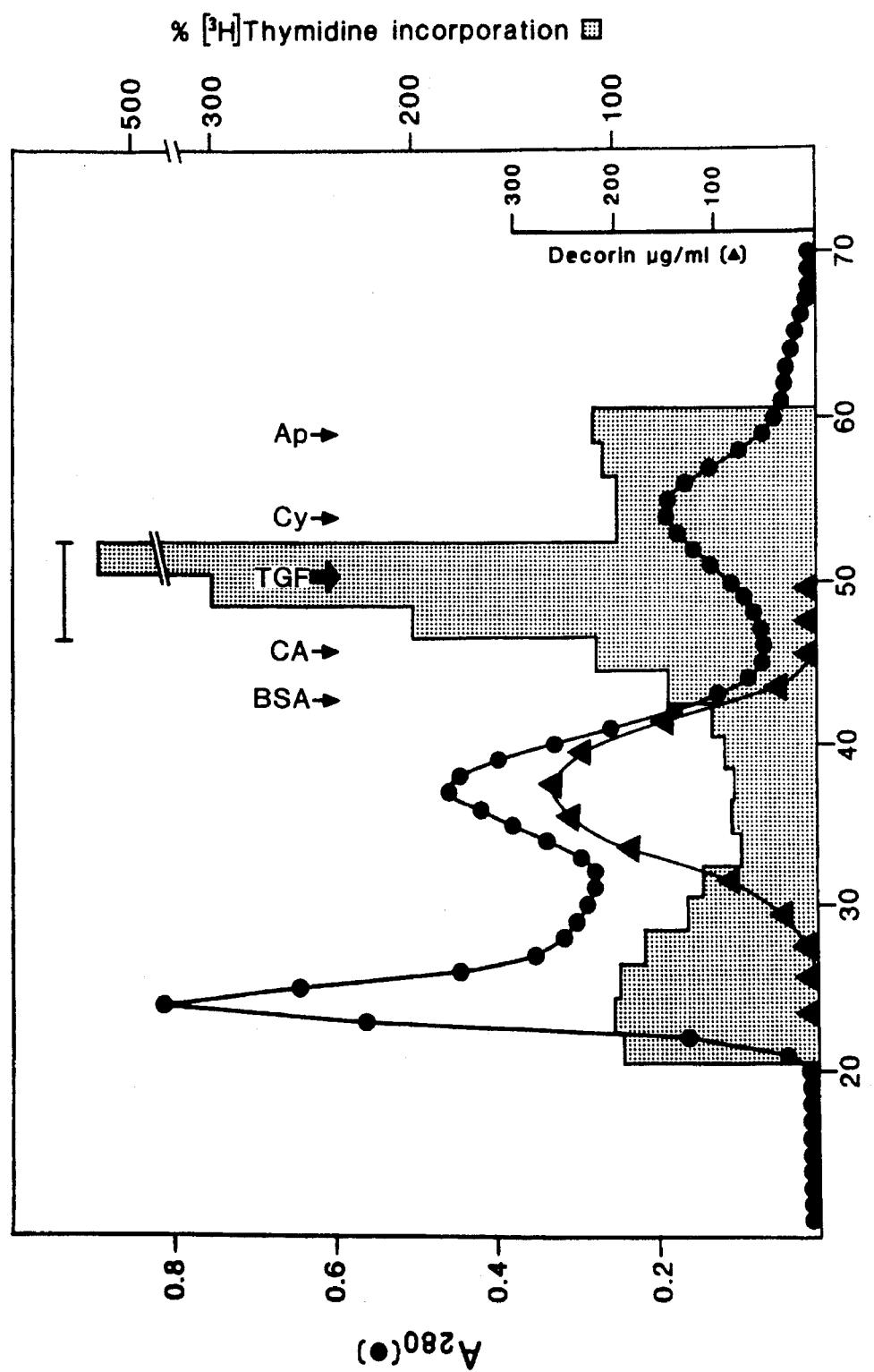
FIG. 5A shows separation of growth inhibitory activity from decorin-expressing CHO cells by gel filtration. Serum-free conditioned medium of decorin overexpressor cells was fractionated by DEAE-Sepharose chromatography in a neutral Tris-HCl buffer and fractions containing growth inhibitory activity were pooled, made 4M with guanidine-HCl and fractionated on a Sepharose CL-6B column equilibrated with the same guanidine-HCl solution. The fractions were analyzed for protein content, decorin content, and growth regulatory activities. Elution positions of marker proteins are indicated by arrows. BSA: bovine serum albumin (Mr=66,000); CA: carbonic anhydrase (Mr=29,000); Cy: cytochrome c (Mr=12,400); Ap: aprotinin (Mr=6,500); TGF: [$^{125}$I]TGFβ1 (Mr=25,000).

Analysis of the decorin contained in the overexpressor culture media not only uncovered the activities of decorin described above, but also revealed the presence of other decorin-associated growth regulatory activities. The overexpressor media were found to contain a TGFβ-like growth inhibitory activity. This was shown by gel filtration of the DEAE-isolated decorin under dissociating conditions. Serum-free conditioned medium of decorin overexpressor CHO-DG44 cells transfected with decorin cDNA was fractionated by DEAE-Sepharose chromatography in a neutral Tris-HCl buffer and fractions containing growth inhibitory activity dialyzed against 50 mM NH$_4$HCO$_3$, lyophilized and dissolved in 4M with guanidine-HCl in a sodium acetate buffer, pH 5.9. The dissolved material was fractionated on a 1.5×70 cm Sepharose CL-6B column equilibrated with the same guanidine-HCl solution. The fractions were analyzed by SDS-PAGE, decorin ELISA and cell growth assays, all described above. Three protein peaks were obtained. One contained high molecular weight proteins such as fibronectin (m.w. 500,000) and no detectable growth regulatory activities, the second was decorin with the activities described under Example III and the third was a low molecular weight (10,000–30,000-dalton) fraction that had a growth inhibitory activity in the mink cell assay and stimulated the growth of the CHO cells. FIG. 5A summarizes these results. Shown are the ability of the gel filtration fractions to affect [$^3$H]-thymidine incorporation by the CHO cells and the concentration of decorin as determined by enzyme immunoassay. Shown also (arrows) are the elution positions of molecular size markers: BSA, bovine serum albumin (Mr=66,000); CA, carbonic anhydrase (Mr=29,000); Cy, cytochrome c (Mr=12,400); AP, aprotinin (Mr=6,500); TGF, [$^{125}$I]TGFβ-1 (Mr=25,000).

The nature of the growth regulatory activity detected in the low molecular weight fraction was examined with an anti-TGFβ-1 antiserum. The antiserum was prepared against a synthetic peptide from residues 78–109 of the human mature TGFβ-1. Antisera raised by others against a cyclic form of the same peptide, the terminal cysteine residues of which were disulfide-linked, have previously been shown to inhibit the binding of TGFβ-1 to its receptors (Flanders et al., Biochemistry 27:739–746 (1988), incorporated by reference herein). The peptide was synthesized in an Applied Biosystems solid phase peptide synthesizer and purified by HPLC. A rabbit was immunized subcutaneously with 2 mg per injection of the peptide which was mixed with 0.5 mg of methylated BSA (Sigma, St. Louis, Mo.) and emulsified in Freund's complete adjuvant. The injections were generally given four weeks apart and the rabbit was bled approximately one week after the second and every successive injection. The antisera used in this work has a titer (50% binding) of 1:6,000 in radioimmunoassay, bound to TGFβ-1 in immunoblots.

Figure 5B:
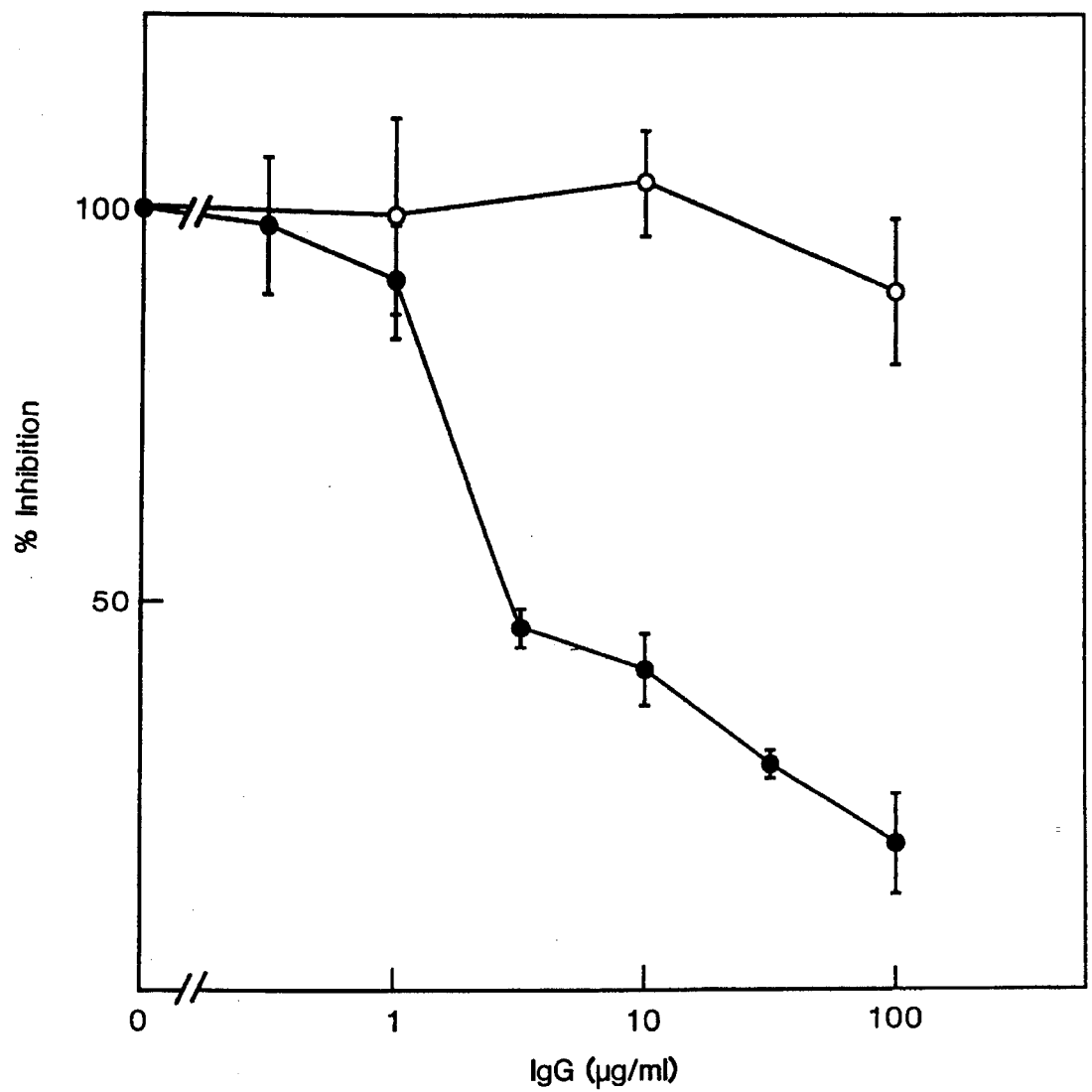
FIG. 5B shows identification of the growth stimulatory material from gel filtration as TGFβ1. The growth stimulatory activity from the late fractions from Sepharose 6B (bar in FIG. 5A) was identified by inhibiting the activity with protein A-purified IgG from an anti-TGFβ antiserum. Data represent percent inhibition of growth stimulatory activity in a [$^3$H]thymidine incorporation assay. Each point shows the mean ±standard deviation of triplicate determinations. Anti-TGFβ1 (●), normal rabbit IgG (○).

This antiserum was capable of inhibiting the activity of purified TGFβ-1 on the CHO cells. Moreover, as shown in FIG. 5B, the antiserum also inhibited the growth stimulatory activity of the low molecular weight fraction as determined by the [$^3$H]-thymidine incorporation assay on the CHO cells. Increasing concentrations of an IgG fraction prepared from the anti-TGFβ-1 antiserum suppressed the stimulatory effect of the low molecular weight fraction in a concentration-dependent manner (●). IgG from a normal rabbit serum had no effect in the assay (○).

Figure 6A:
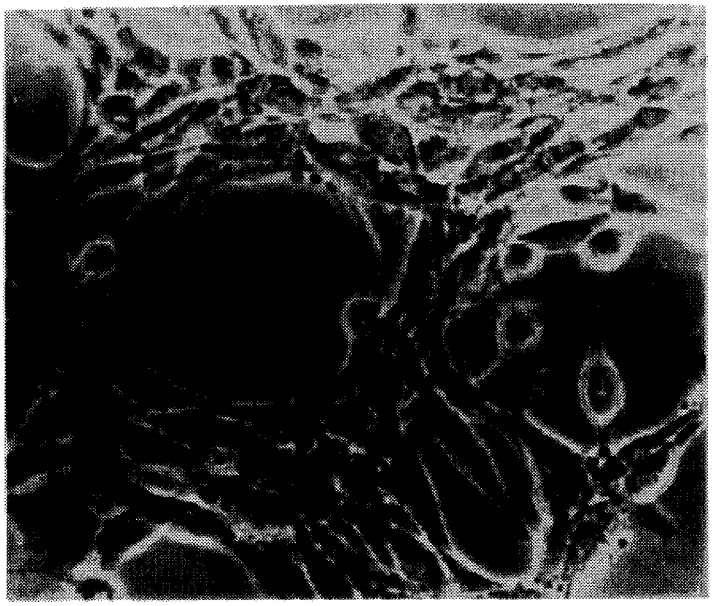
FIGS. 6A and 6B show micrographs demonstrating a decorin-binding cell regulatory activity that is not suppressed by antibodies to TGFβ-1.
Figure 6B:
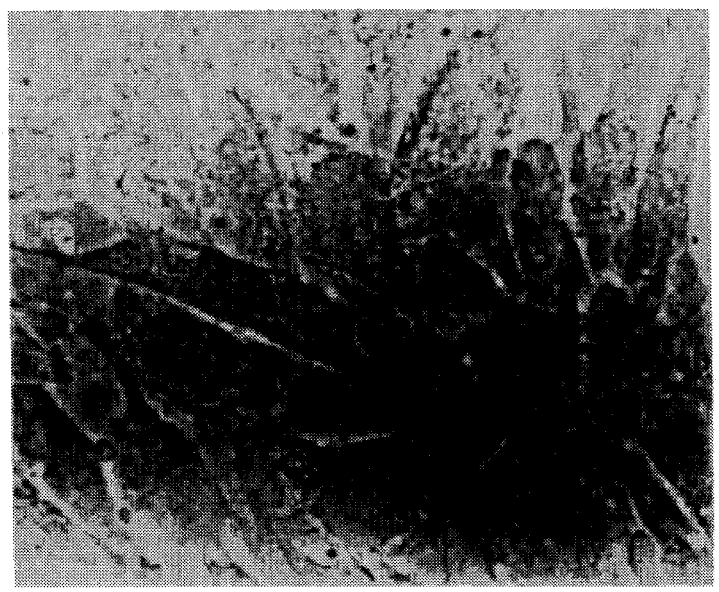

The above result identified the stimulatory factor in the low molecular weight fraction as TGFβ-1. However, TGFβ-1 is not the only active compound in that fraction. Despite the restoration of thymidine incorporation by the anti-TGFβ-1 antibody shown in FIG. 5B, the cells treated with the low molecular weight fraction were morphologically different from the cells treated with the control IgG or cells treated with antibody alone. This effect was particularly clear when the antibody-treated, low molecular weight fraction was added to cultures of H-ras transformed NIH 3T3 cells (Der et al., Proc. Natl. Acado Sci. USA 79:3637–3640 (1982)). As shown in FIGS. 6A and 6B, cells treated with the low molecular weight fraction and antibody (micrograph in panel B) appeared more spread and contact inhibited than the control cells (micrograph in panel A). This result shows that the CHO cell-derived recombinant decorin is associated with a cell regulatory factor, MRF, distinct from the well characterized TGFβ's.

Additional evidence that the new factor is distinct from TGFβ-1 came from HPLC experiments. Further separations of the low molecular weight from the Sepharose CL-6B column was done on a Vydac C4 reverse phase column (1×25 cm, 5 µm particle size, the Separations Group, Hesperia, Calif.) in 0.1% trifluoroacetic acid. Bound proteins were eluted with a gradient of acetonitrite (22–40%) and the factions were assayed for growth-inhibitory activity in the mink lung epithelial cells and MRF activity in H-ras 3T3 cells. The result showed that the TGFβ-1 activity eluted at the beginning of the gradient, whereas the MRF activity eluted toward the end of the gradient.

The deposit of the CHO-DG44 cells transfected with pSV2-decorin was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from date of deposit. The deposits will be made available by ATCC under the terms of the Budapest Treaty, and subject to an agreement between Applicants and ATCC which assures permanent and unrestricted availability upon issuance of the pertinent U.S. patent. The Assignee herein agrees that if the culture on deposit should die or be lost or destroyed when cultivated under suitable conditions, it will be promptly replaced upon notification with a viable specimen of the same culture. Availability of the deposits is not to be construed as a license to practice the invention in contravention of the rights granted under the authority of any government in accordance with its patent laws.

The deposit was made for the convenience of the relevant public and does not constitute an admission that a written description would not be sufficient to permit practice of the invention to the specific construct. Set forth hereinabove is a complete written description enabling a practitioner of ordinary skill to duplicate the construct deposited and to construct alternative forms of DNA, or organisms containing it, which permit practice of the invention as claimed.

Although the invention has been described with reference to the presently-preferred embodiments, it should be understood that various modifications can be made without departing from the spirit of the invention. Accordingly, the invention is limited only by the following claims.

What is claimed is:

1. A method of inhibiting an activity of TGFβ, comprising contacting TGFβ with an effective amount of purified decorin.

2. The method of claim 1, wherein the TGFβ is TGFβ-1.

3. The method of claim 1, wherein the TGFβ is TGFβ-2.

4. The method of claim 1, wherein the inhibited activity is promotion of cell proliferation.

5. The method of claim 1, wherein the inhibited activity is suppression of cell proliferation.

6. The method of claim 1, wherein the activity is promotion of extracellular matrix production.

\* \* \* \* \*

UNITED STATES PATENT AND TRADEMARK OFFICE
CERTIFICATE OF CORRECTION

PATENT NO. : 5,583,103
DATED : December 10, 1996
INVENTOR(S) : Ruoslahti et al.

It is certified that error appears in the above-identified patent and that said Letters Patent is hereby corrected as shown below:

In column 1, line 11, please delete "continuation of" and replace therefor with --continuation-in-part of--.

In column 7, line 24, please delete "Culture" and replace with --Cultures--.

In column 8, line 55, please delete "36:244246" and replace therefor with --36:244-246--.

In column 9, line 8, please delete "50 mMTris/HCl," and replace therefor with --50 mM Tris/HCl,--.

In column 9, line 22, please delete "e MEM" and replace with --αMEM--.

In column 9, line 62, please delete "(574)" and replace with --(●)--.

In column 12, line 26, please delete "MvLu" and replace with --MvlLu--.

In column 13, line 51, please delete "Acado" and replace with --Acad.--.

Signed and Sealed this

Second Day of March, 1999

Attest:

Attesting Officer

Q. TODD DICKINSON

Acting Commissioner of Patents and Trademarks